(12) United States Patent
Derakhshan et al.

(10) Patent No.: US 11,071,608 B2
(45) Date of Patent: Jul. 27, 2021

(54) MATCHING ASSETS IN 3D TREATMENT PLANS

(71) Applicant: Align Technology, Inc., San Jose, CA (US)

(72) Inventors: Mitra Derakhshan, Herndon, VA (US); Sophie Acker, Amsterdam (NL); Susanne Reichart, Amsterdam (NL)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/385,262

(22) Filed: Dec. 20, 2016

(65) Prior Publication Data

US 2018/0168775 A1 Jun. 21, 2018

(51) Int. Cl.
| | |
|---|---|
| *A61C 7/00* | (2006.01) |
| *G16H 20/30* | (2018.01) |
| *G16H 50/20* | (2018.01) |
| *A61C 7/08* | (2006.01) |

(52) U.S. Cl.
CPC ............. *A61C 7/002* (2013.01); *G16H 20/30* (2018.01); *G16H 50/20* (2018.01); *A61C 7/08* (2013.01)

(58) Field of Classification Search
CPC ................ A61C 7/002; A61C 13/0004; A61C 2007/004
See application file for complete search history.

(56) References Cited

U.S. PATENT DOCUMENTS

| | | |
|---|---|---|
| 2,467,432 A | 4/1949 | Kesling |
| 3,407,500 A | 10/1968 | Kesling |
| 3,600,808 A | 8/1971 | Reeve |
| 3,660,900 A | 5/1972 | Andrews |
| 3,683,502 A | 8/1972 | Wallshein |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23, 1980, Los Angeles, CA, p. 195.
(Continued)

*Primary Examiner* — Nicholas D Lucchesi
*Assistant Examiner* — Hao D Mai
(74) *Attorney, Agent, or Firm* — Wilson Sonsini Goodrich & Rosati

(57) ABSTRACT

A method for treating malocclusions of a patient's teeth includes receiving an initial position of a patient's teeth and a target position of the patient's teeth. The method also includes determining a treatment plan to reposition the patient's teeth towards the target position. The method also includes receiving treatment strategies for the patient's teeth based at least in part of the treatment plan and matching the initial position of the patient's teeth, the target position of a patient's teeth, and the treatment strategies for the patient's teeth with initial positions, target positions, and treatment strategies of a plurality of existing cases. The method also includes sending the matched cases to a dental practitioner including matched educational assets.

20 Claims, 8 Drawing Sheets

(56) References Cited

U.S. PATENT DOCUMENTS

| | | |
|---|---|---|
| 3,738,005 A | 6/1973 | Cohen et al. |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | Van Der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley et al. |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre, Sr. |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | Van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,450,807 B1 | 9/2002 | Chishti et al. |
| 6,482,298 B1 | 11/2002 | Bhatnagar |
| 6,524,101 B1 | 2/2003 | Phan et al. |
| 6,554,611 B2 | 4/2003 | Shishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,722,880 B2 | 4/2004 | Chishti et al. |
| 6,830,450 B2 | 12/2004 | Knopp et al. |
| 2002/0006597 A1 | 1/2002 | Andreiko et al. |
| 2003/0009252 A1 | 1/2003 | Pavlovskaia et al. |
| 2003/0139834 A1 | 7/2003 | Nikolskiy et al. |
| 2003/0224311 A1 | 12/2003 | Cronauer |
| 2004/0128010 A1 | 7/2004 | Pavlovskaia et al. |

(56) References Cited

U.S. PATENT DOCUMENTS

| | | | |
|---|---|---|---|
| 2005/0038669 A1* | 2/2005 | Sachdeva | G06F 19/3481 705/2 |
| 2005/0055118 A1 | 3/2005 | Nikolskiy et al. | |
| 2009/0132455 A1* | 5/2009 | Kuo | A61C 7/00 706/46 |

FOREIGN PATENT DOCUMENTS

| | | |
|---|---|---|
| AU | 5598894 A | 6/1994 |
| CA | 1121955 A | 4/1982 |
| DE | 2749802 A1 | 5/1978 |
| DE | 69327661 T2 | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 1/2000 |
| EP | 0774933 B1 | 12/2000 |
| EP | 0731673 B1 | 5/2001 |
| ES | 463897 A1 | 1/1980 |
| FR | 2369828 A1 | 6/1978 |
| FR | 2652256 A1 | 3/1991 |
| GB | 1550777 A | 8/1979 |
| JP | S5358191 A | 5/1978 |
| JP | H0428359 A | 1/1992 |
| JP | H08508174 A | 9/1996 |
| WO | WO-9008512 A1 | 8/1990 |
| WO | WO-9104713 A1 | 4/1991 |
| WO | WO-9410935 A1 | 5/1994 |
| WO | WO-9832394 A1 | 7/1998 |
| WO | WO-9844865 A1 | 10/1998 |
| WO | WO-9858596 A1 | 12/1998 |

OTHER PUBLICATIONS

Alcaniz, et aL, "An Advanced System for the Simulation and Planning of Orthodontic Treatments," Karl Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990).

Altschuler, "3D Mapping of Maxillo-Facial Prosthesis," AADR Abstract #607, 2 pages total, (1980).

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging Applications for Automated Industrial Inspection and Assembly, vol. 182, p. 187-191 (1979).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "Integrated Three-Dimensional Craniofacial Mapping: Background, Principles, and Perspectives," Semin. in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff, "Computerized Diagnostic Setups and Simulations," Angle Orthod., 40(1):28-36 (Jan. 1970).

Biggerstaff et al., "Computerized Analysis of Occlusion in the Postcanine Dentition," Am. J. Orthod., 61(3): 245-254 (Mar. 1972).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004.

Bourke, "Coordinate System Transformation," (Jun. 1996), p. 1, retrieved from the Internet Nov. 5, 2004, URL< http://astronomy.swin.edu.au/—pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: Comparison with Manual Measurements of Mesio-distal Diameter," J. Dent. Res., 65(3):428-431 (Mar. 1986).

Burstone et al., Precision Adjustment of the Transpalatal Lingual Arch: Computer Arch Form IN Predetermination, Am, Journal of Orthodontics, vol. 79, No. 2 (Feb. 1981), pp. 115-133.

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979).

Cardinal Industrial Finishes, Powder Coatings information posted at<http://www.cardinalpaint.com> on Aug. 25, 2000, 2 pages.

Carnaghan, "An Alternative to Holograms for the Portrayal of Human Teeth," 4th Int'l. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does it Work?", Canadian Dental Journal, vol. 57, No. 2, pp. 121-123 (Feb. 1991).

Crawford, "Computers in Dentistry: Part 1 CAD/CAM: The Computer Moves Chairside, Part 2 F. Duret—A Man with a Vision, Part 3 the Computer Gives New Vision—Literally, Part 4 Bytes 'N Bites—The Computer Moves from the Front Desk to the Operatory," Canadian Dental Journal, vol. 54 (9), pp. 661-666 (1988).

Crooks, "CAD/CAM Comes to USC," USC Dentistry, pp. 14-17 (Spring 1990).

(56) References Cited

OTHER PUBLICATIONS

Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin. Orthod., 7(4):258-265 (Dec. 2001).
Cutting et a/., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production AG, pp. 1-7 (Jan. 1992).
Definition for gingiva. Dictionary.com p. 1-3. Retrieved from the internet Nov. 5, 2004<http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium JD on Computer Restorations: State of the Art of the CEREC-Method, May 1991, 2 pages total.
Dentrac Corporation, Dentrac document, pp. 4-13 (1992).
Dent-X posted on Sep. 24, 1998 at< http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al., "CAD/CAM Imaging in Dentistry," Curr. Opin. Dent., 1:150-154 (1991).
Duret et al, "CAD-CAM in Dentistry," J. Am. Dent. Assoc. 117:715-720 (Nov. 1988).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et a/., "Automated Finite Element Modeling of a Human Mandible with Dental Implants," JS WSCG '98—Conference Program, retrieved from the Internet:<http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James a. McNamura, Jr., on the Frankel Appliance: Part 2: Clinical 1-1 Management, "J. Clin. Orthod., 16(6):390-407 (Jun. 1982).
Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et a/., "Computer-Based Image Analysis of Artificial Root Surface Caries," Abstracts of Papers, J. Dent. Res., 70:528 (Apr. 17-21, 1991).
Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressputonfa . . . >.
Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), Informatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999). 0.
Important Tip About Wearing the Red White & Blue Active Clear Retainer System, Allesee Orthodontic Appliances—Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
JP Faber et al., "Computerized Interactive Orthodontic Treatment Planning," Am. J. Orthod., 73(1):36-46 (Jan. 1978).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling, Coordinating the Predetermined Pattern and Tooth Positioner with Conventional Treatment, KN Am. J. Orthod. Oral Surg. (1946) 32:285-293.
Kesling et al., The Philosophy of the Tooth Positioning Appliance, American Journal of Orthodontics and Oral surgery. 1945; 31:297-304.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984).
KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).

(56) References Cited

OTHER PUBLICATIONS

Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventors CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7; 28 (1993).
Proffit et al., Contemporary Orthodontics, (Second Ed.), Chapter 15, Mosby Inc., pp. 470-533 (Oct. 1993.
Raintree Essix & ARS Materials, Inc., Raintree Essix, Technical Magazine Table of contents and Essix Appliances,< http:// www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art'?", J. Amer. Dent. Assoc., 122:43-48 1991.
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.

Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice is Clear: Red, White & Blue . . . The Simple, Affordable, No-Braces Treatment, Allesee HI Orthodontic Appliances—Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances—Pro Lab product information for patients,<http://ormco.com/aoa/appliancesservices/RWB/patients.html>, 2 pages (May 19, 2003).
The Choice is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20,1997, 41 pages total.
Van Der Linden, "A New Method to Determine Tooth Positions and Dental Arch Dimensions," J. Dent. Res., 51(4):1104 (Jul.-Aug. 1972).
Van Der Linden et al., "Three-Dimensional Analysis of Dental Casts by Means of the Optocom," J. Dent. Res., p. 1100 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).

(56) References Cited

OTHER PUBLICATIONS

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).

Yoshii, "Research on a New Orthodontic Appliance: the Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III. The General Concept of the D.P. Method and its Therapeutic Effect, Part 1, Dental and Functional Reversed Occlusion Case Reports," Nippon Dental Review, 457:146-164 (Nov. 1980).

Yoshii, "Research on a New Orthodontic Appliance: The Dynamic Positioner (D.P.); III.—The General Concept of the D.P. Method and its Therapeutic Effect, Part 2. Skeletal Reversed Occlusion Case Reports," Nippon Dental Review, 458:112-129 (Dec. 1980).

You May Be a Candidate for This Invisible No-Braces Treatment, Allesee Orthodontic Appliances—Pro Lab product information for patients, 2 pages (2002).

\* cited by examiner

MATCHING ASSETS IN 3D TREATMENT PLANS

FIELD OF THE INVENTION

This disclosure is related generally to the field of dentistry and orthodontics. More specifically, this disclosure is related to methods and systems for matching assets to orthodontic assessments and treatment plans.

BACKGROUND

One objective of orthodontics is to realign patients' teeth to positions where the teeth function optimally and have an aesthetic appearance. The goal of a dental practitioner is to take the patient from their current condition also referred to as an initial or starting dentition, arrangement, or malocclusion to, or towards, a final condition, arrangement, or treatment goal. The result achieved is known as the treatment outcome. A dental practitioner has may have many alternative or complementary treatment options or strategies for a patient to move the patient's teeth towards the treatment goal. A treatment plan includes the various selected methodologies used by the dental practitioner to move the patient's teeth towards the treatment goal.

Typically, appliances such as fixed braces and wires are applied to a patient's teeth to gradually reposition them from an initial arrangement to a final arrangement. The diagnosis and treatment planning process of orthodontic cases can be imprecise as the final dentition of a patient is based on the knowledge and expertise of the treating dental practitioner in assembling various parameters in an assessment of each patient's condition and in a determination of a final position for each tooth. Different clinicians will vary in their definitions of individual orthodontic parameters and their definition of how a case should ideally be treated will also often vary.

Dental practitioners may use different methods of moving teeth towards a treatment goal, based on their personal past experiences with the various options for moving teeth from particular starting arrangement towards a particular desired final condition. Dental practitioners may be unaware of or unfamiliar with some approaches for moving teeth because the approach is new, perceived as difficult, only applies is rarely encountered situations, or for other reasons.

In view of the foregoing, it would be desirable to have methods and systems for matching assets, such as existing cases, including past cases and presently pending cases, and educational materials to orthodontic assessments and treatment plans.

SUMMARY

Improved systems and methods for repositioning a patient's teeth are provided herein.

A method for treating malocclusions of a patient's teeth is disclosed. The method may comprise receiving an initial position of a patient's teeth; receiving a target position of the patient's teeth; determining a treatment plan to reposition the patient's teeth towards the target position; receiving treatment strategies for the patient's teeth based at least in part of the treatment plan; matching the initial position of the patient's teeth, the target position of a patient's teeth, and the treatment strategies for the patient's teeth with initial positions, target positions, and treatment strategies of a plurality of existing cases; and sending the matched cases to a dental practitioner.

In some embodiment the method may include receiving patient factors for the patient, wherein the matching comprises matching the patient factors for the patient with patient factors of the plurality of existing cases. The patient factors may include one or more of age, sex, ethnicity, and race. The patient factors may include one or more of tooth shape, tooth size, tooth morphology, and arch shape. The treatment strategies may include or more of tooth extraction, elastics use, attachment use, staging, and class II correction. The target position may be an intermediate position of the patient's teeth during treatment. The target position may be a desired position of the patient's teeth at the end of treatment.

The matching may include binary matching of at least one of the initial position of the patient's teeth, the target position of a patient's teeth, and the treatment strategies for the patient's teeth with initial positions, target positions, and treatment strategies of a plurality of existing cases. The matching may include matching includes determining a degree of match of at least one of the initial position of the patient's teeth, the target position of a patient's teeth, and the treatment strategies for the patient's teeth with initial positions, target positions, and treatment strategies of a plurality of existing cases. The matching may include matching includes averaging the degree of match of at least one of the initial position of the patient's teeth, the target position of a patient's teeth, and the treatment strategies for the patient's teeth with initial positions, target positions, and treatment strategies of a plurality of existing cases.

The method may include ranking the existing cases based on the matching. The ranking may include selecting existing cases based on their ranking and providing the selected existing cases to the dental professional. The method may include providing at least three cases from the five highest ranked existing cases and providing the three selected existing cases to the dental professional.

A method of treating malocclusions of a patient's teeth is disclosed. The method may comprise receiving initial and target positions of a patient's teeth; receiving treatment strategies for moving the patient's teeth from the initial position towards a target position; receiving patient factors; matching the initial position, target position, treatment strategies and patient factors with initial position, target position, treatment strategies and patient factors of existing cases; and providing the matching cases to a dental practitioner.

The method may include receiving patient factors for the patient, and wherein the matching comprises matching the patient factors for the patient with patient factors of the plurality of existing cases. The patient factors may include one or more of age, sex, ethnicity and race. The patient factors may include one or more of tooth shape, tooth size, tooth morphology, and arch shape. The treatment strategies may include or more of tooth extraction, elastics use, attachment use, staging, and class II correction. The target position is an intermediate position of the patient's teeth during treatment. The target position may be a desired position of the patient's teeth at the end of treatment.

The matching may include binary matching of at least one of the initial position of the patient's teeth, the target position of a patient's teeth, and the treatment strategies for the patient's teeth with initial positions, target positions, and treatment strategies of a plurality of existing cases. The matching includes matching may include determining a degree of match of at least one of the initial position of the patient's teeth, the target position of a patient's teeth, and the treatment strategies for the patient's teeth with initial positions, target positions, and treatment strategies of a plurality of existing cases. The matching includes matching may include averaging the degree of match of at least one of the initial position of the patient's teeth, the target position of a patient's teeth, and the treatment strategies for the patient's teeth with initial positions, target positions, and treatment strategies of a plurality of existing cases. The method may include raking the existing cases based on the matching.

The ranking may include selecting existing cases based on their ranking and providing the selected existing cases to the dental professional. The method may include providing at least three cases from the five highest ranked existing cases and providing the three selected existing cases to the dental professional.

In some aspects a method of treating malocclusions of a patient's teeth is disclosed. The method may comprise receiving initial and target positions of a patient's teeth; receiving treatment strategies for moving the patient's teeth from the initial position towards a target position; receiving dental practitioner factors of a dental practitioner; matching the initial position, target position, treatment strategies and patient factors with educational assets; and providing the educational assets to the dental practitioner.

The method may include receiving patient factors for the patient, and wherein the matching comprises matching the patient factors for the patient with patient factors of the plurality of existing cases. The patient factors may include one or more of age, sex, ethnicity, and race. The patient factors may include one or more of tooth shape, tooth size, tooth morphology, and arch shape. The treatment strategies may include or more of tooth extraction, elastics use, attachment use, staging, and class II correction. The target position may be an intermediate position of the patient's teeth during treatment. The target position may be a desired position of the patient's teeth at the end of treatment.

The matching may include binary matching of the initial position, target position, treatment strategies and patient factors with educational assets. The matching may include matching includes determining a degree of match of the initial position, target position, treatment strategies and patient factors with educational assets. The method may include raking the existing cases based on the matching. The method may include providing ranking includes selecting existing cases based on their ranking and providing the selected existing cases to the dental professional. The method may include providing at least three cases from the five highest ranked existing cases and providing the three selected existing cases to the dental professional.

In some aspects a system for treating malocclusions of a patient's teeth is disclosed. The system my comprise a receiver to receive an initial position of a patient's teeth and a target position of the patient's teeth; a processor configured to determine a treatment plan to reposition the patient's teeth towards the target position, determine treatment strategies for the patient's teeth based at least in part of the treatment plan, and match the initial position of the patient's teeth, the target position of a patient's teeth, and the treatment strategies for the patient's teeth with initial positions, target positions, and treatment strategies of a plurality of existing cases; and an interface configured to provide the matched cases to a dental practitioner. Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
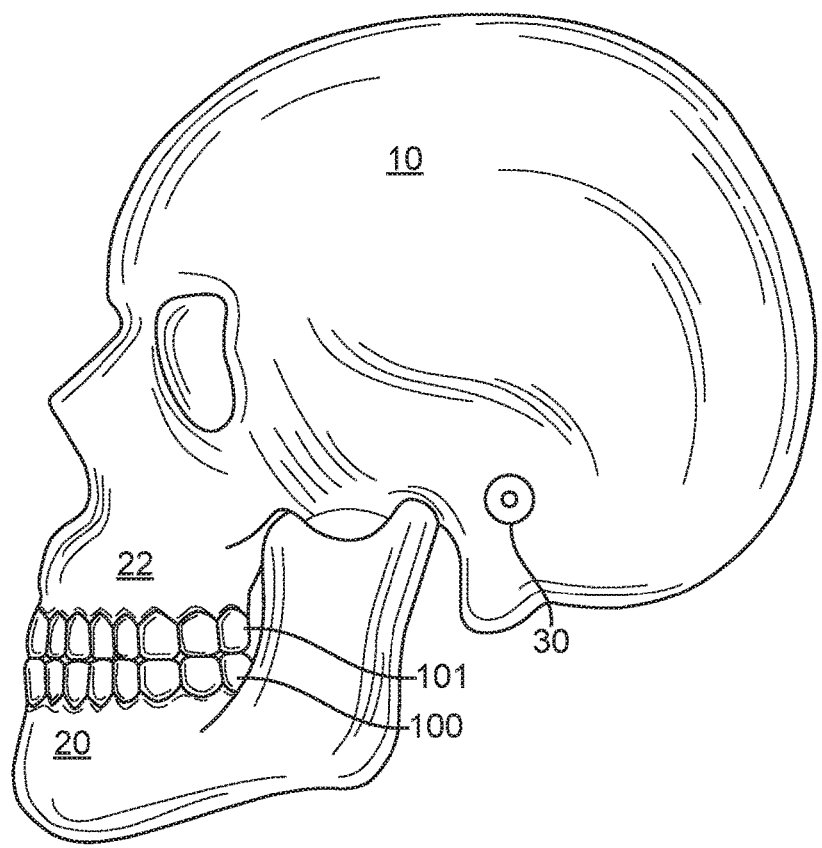
FIG. 1 is an elevational diagram showing the anatomical relationship of the jaws of a patient, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the disclosure as described herein.

As used herein the terms "dental appliance." "orthodontic appliance." and "tooth receiving appliance" are treated synonymously.

As used herein the term "and/or" is used as a functional word to indicate that two words or expressions are to be taken together or individually. For example, A and/or B encompasses A alone, B alone, and A and B together.

As used herein a "plurality of teeth" encompasses two or more teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The present disclosure provides orthodontic systems and related methods for providing improved or more effective tooth moving systems for eliciting a desired tooth movement and/or repositioning teeth into a desired arrangement.

The embodiments disclosed herein are well suited for combination with one or known commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration.

The force generating components disclosed herein can generate forces based on a target tooth displacement or orientation. For example, an amount of tooth displacement can be selected, and the force generating component can be fabricated such that a tooth displacement force is generated when the appliance is worn, so long as the amount of tooth displacement is less than the target tooth displacement. Thus, an appliance can generate tooth displacement forces without causing excessive tooth displacement. In some cases, the target tooth displacement can be adjustable; for example, adjustable screws, springs, bands, or other components can be adjusted to change the size of the aligner, thereby changing the target tooth displacement. An adjustable aligner can be used to generate a slow tooth displacement, for example.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Turning now to the drawings. FIG. 1 shows a skull 10 with an upper jawbone 22 and a lower jawbone 20. The lower jawbone 20 hinges at a joint 30 to the skull 10. The joint 30 is called a temporomandibular joint (TMJ). The upper jawbone 22 is associated with an upper jaw 101, while the lower jawbone 20 is associated with a lower jaw 100.

A computer model of the jaws 100 and 101 can be generated, and a computer simulation models interactions among the teeth on the jaws 100 and 101. The computer simulation can allow the system to focus on motions involving contacts between teeth mounted on the jaws. The computer simulation can allow the system to render realistic jaw movements which are physically correct when the jaws 100 and 101 contact each other. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions can be determined for one jaw, but may also be determined for both jaws to represent the bite.

Figure 2A:
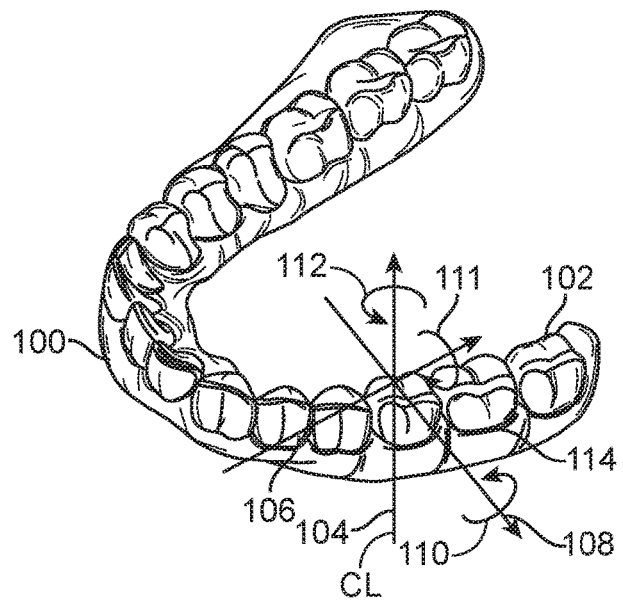
FIG. 2A shows in more detail the patient's lower jaw and provides a general indication of how teeth may move, in accordance with embodiments.

Referring now to FIG. 2A, the lower jaw 100 includes a plurality of teeth 102, for example. At least some of these teeth may be moved from an initial tooth arrangement to a subsequent tooth arrangement. As a frame of reference describing how a tooth has been moved, an arbitrary centerline (CL) may be drawn through the tooth 102. With reference to this centerline (CL), each tooth movement may be tracked in orthogonal directions represented by axes 104, 106, and 108 (where 104 is the centerline). The tooth may be rotated about the axis 108 (angulation), axis 106 (proclination), and the axis 104 (rotation) as indicated by arrows 110, 111, and 112, respectively. Additionally, the tooth may be rotated about the centerline. Thus, all possible free-form motions of the tooth can be tracked. These motions include translation (e.g., movement in one or more of the X-axis or Y-axis), rotation (e.g., movement about the Z-axis), intrusion and extrusion (e.g., movement in the Z-axis), or tipping (e.g., movement about one or more of the X-axis or Y-axis), to name a few. In addition to teeth movement, the movement of the gum line 114 may also be tracked using models such as model 100. In some embodiments, the model includes X-ray information of the jaw so that movements of the roots of the teeth can be tracked as well.

Figure 2B:
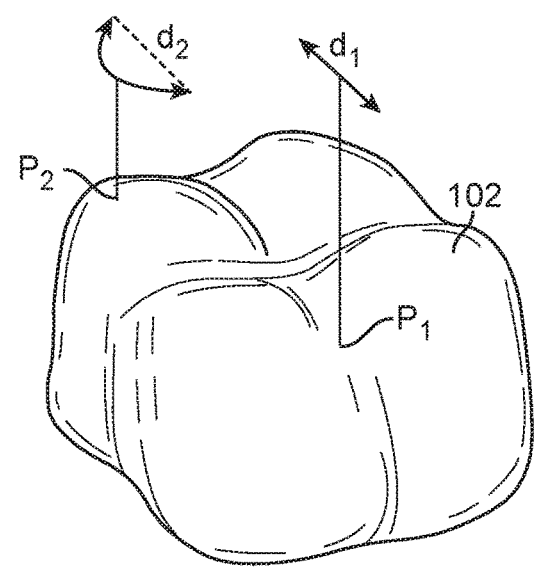
FIG. 2B shows a single tooth from FIG. 2A and defines how tooth movement distances can be determined, in accordance with embodiments.

FIG. 2B shows how the magnitude of any tooth movement may be defined in terms of a maximum linear translation of any point P on a tooth 102. Each point P1 may undergo a cumulative translation as that tooth is moved in any of the orthogonal or rotational directions defined in FIG. 2A. That is, while the point will usually follow a nonlinear path, there can be a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present disclosure may be defined in terms of the maximum permissible movement of a point P1 induced on any particular tooth. Such maximum tooth movement, in turn, can be defined as the maximum linear translation of that point P1 on the tooth which undergoes the maximum movement for that tooth in any treatment step. In embodiments where the orthodontic treatment includes a temporal series of treatment steps, the tooth velocity can be defined as the maximum movement per treatment step. Each treatment step can be defined as the duration each orthodontic appliance is worn (e.g., 1 to 2 weeks).

Figure 3A:
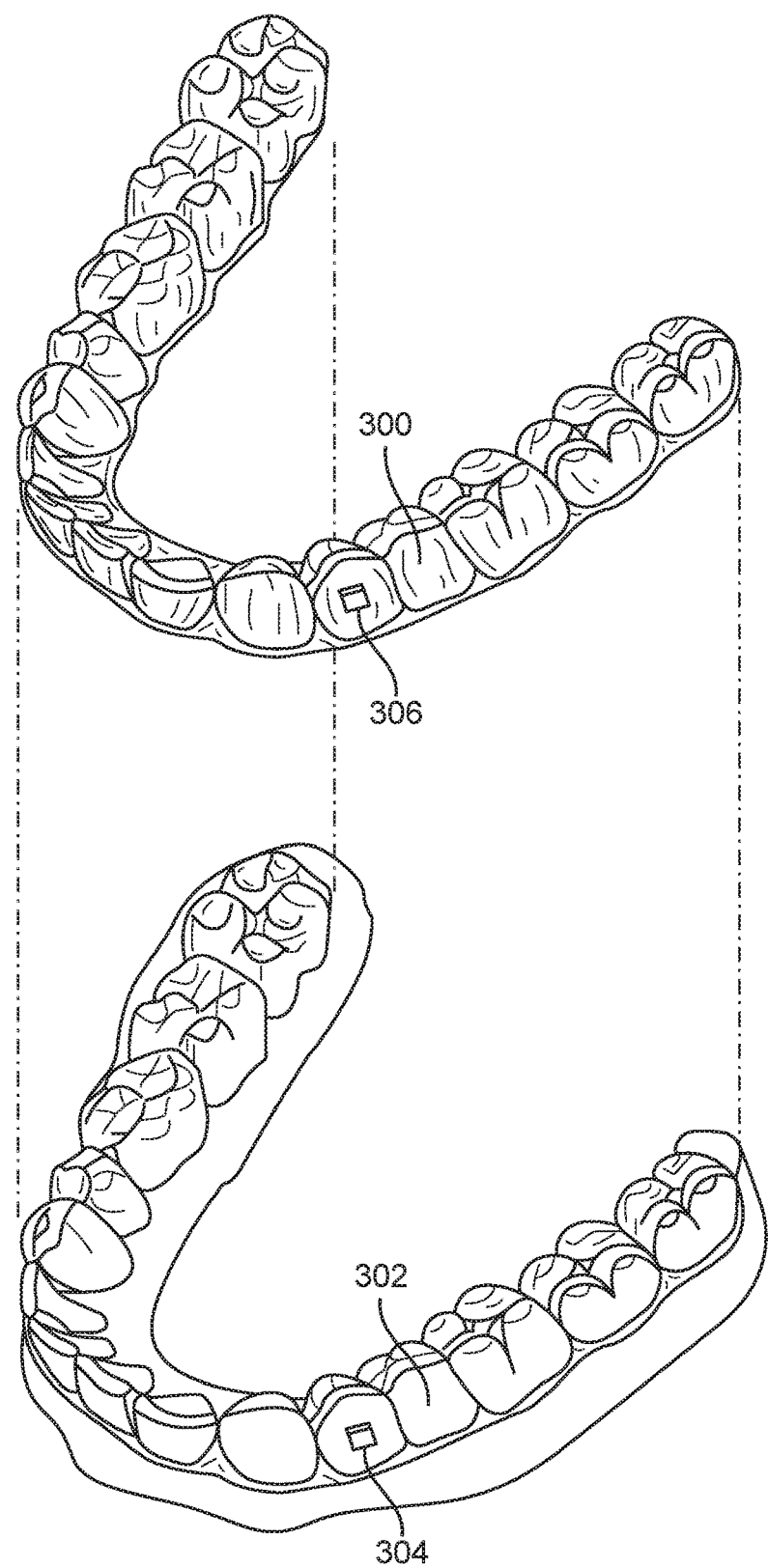
FIG. 3A illustrates a tooth repositioning appliance, in accordance with embodiments.

The present disclosure provides various orthodontic treatment procedures in which tooth movement is achieved through placement of one or more orthodontic appliances on a patient's teeth. Appliances having teeth receiving cavities that receive and reposition teeth. e.g., via application of force due to appliance resiliency, are generally illustrated with regard to FIG. 3A. FIG. 3A illustrates an exemplary tooth repositioning appliance or aligner 300 that can be worn by a patient in order to achieve an incremental repositioning of individual teeth 302 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 304 on teeth 302 with corresponding receptacles or apertures 306 in the appliance 300 so that the appliance can apply a selected force on the tooth. Exemplary appliances, including those utilized in the Invisalign® System, are described in numerous patents and patent applications assigned to Align Technology. Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309, 215 and 6,830,450.

Figure 3B:
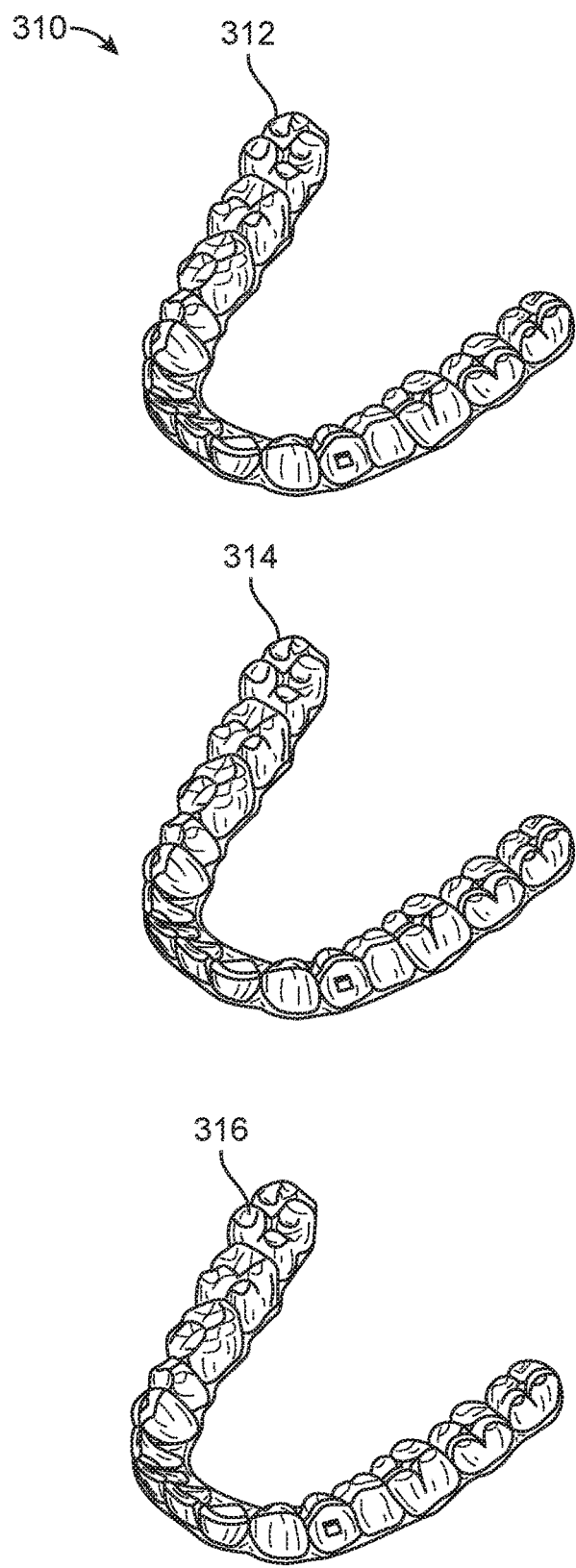
FIG. 3B illustrates a tooth repositioning system, in accordance with embodiments.

FIG. 3B illustrates a tooth repositioning system 310 including a plurality of appliances 312, 314, 316. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 310 can include a first appliance 312 corresponding to an initial tooth arrangement, one or more intermediate appliances 314 corresponding to one or more intermediate arrangements, and a final appliance 316 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 3A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein.

Tooth movement of the crown greater than the movement of the root can be referred to as tipping. Equivalent movement of the crown and root can be referred to as translation. Movement of the root greater than the crown can be referred to as root movement.

Figure 3C:
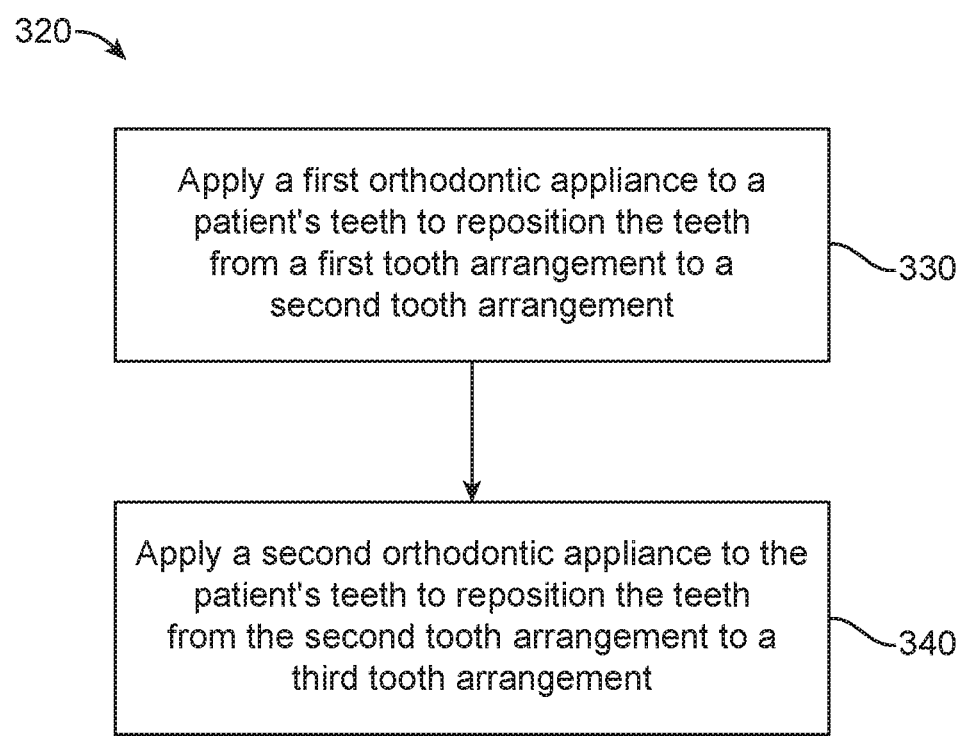
FIG. 3C illustrates a method of orthodontic treatment using a plurality of appliances, in accordance with embodiments.

FIG. 3C illustrates a method 320 of orthodontic treatment using a plurality of appliances, in accordance with embodiments. The method 320 can be practiced using any of the appliances or appliance sets described herein. In step 330, a first orthodontic appliance is applied to a patient's teeth in order to reposition the teeth from a first tooth arrangement to a second tooth arrangement. In step 340, a second orthodontic appliance is applied to the patient's teeth in order to reposition the teeth from the second tooth arrangement to a third tooth arrangement. The method 320 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 4:
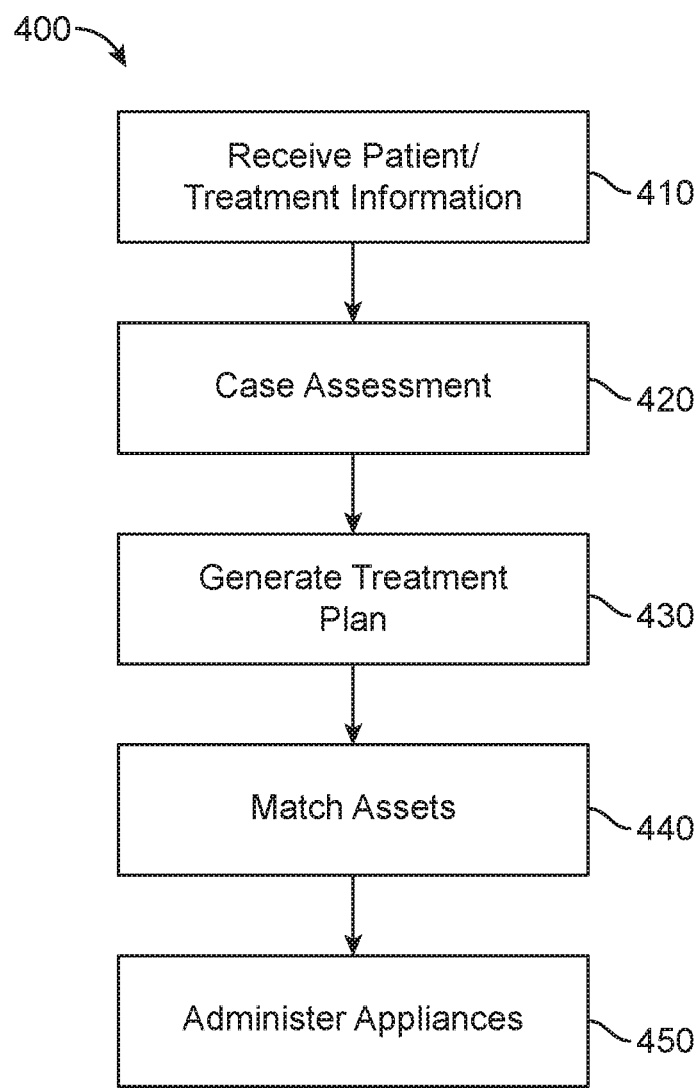
FIG. 4 illustrates a method of treating a patient.

Referring to FIG. 4, a process 400 according to the present disclosure is illustrated. The process 400 includes receiving information regarding the orthodontic condition of the patient and/or treatment information at block 410, generating an assessment of the case at block 420, and generating a treatment plan for repositioning a patient's teeth and block 430. Briefly, patient/treatment information can include obtaining data comprising an initial arrangement of the patient's teeth, which typically includes obtaining an impression or scan of the patient's teeth in their initial positions prior to the onset of treatment and can further include identification of one or more treatment goals selected by the practitioner and/or patient. The patient information can include information such as patient demographic factors, such as age, gender, ethnicity, and race. These factors may help to information the treatment plan because age, gender, and race can all have an impact on how tooth treatment progresses and the effects of treatment. For example, some ages, races, and genders, may respond more or less quickly to certain treatments. Other patient information may include patient tooth factors, such as tooth shape, tooth size, or morphology, arch shape, or cephalometrics, among others. These factors can have an effect on how forces are applied to the teeth, for example, some tooth shapes may not move as desired when force is applied with standard aligners. In such situations attachments may be added to the teeth and attachment receiving wells may be added to the aligners to more effectively impart movement forces onto the patient's tooth.

A case assessment can be generated so as to assess the complexity or difficulty of moving the particular patient's teeth in general or specifically corresponding to identified treatment goals, and may further include practitioner experience and/or comfort level in administering the desired orthodontic treatment. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The case assessment and treatment plan may include various treatment strategies, such as staging the movement of teeth in ordered steps to prevent collisions, tooth rotation or translation strategies, interproximal reduction of one or more teeth, and other treatment strategies.

In some embodiments, the treatment strategies are provided by the dental practitioner and the practitioner receives a treatment plan. In some embodiments, the dental practitioner may provide one or more of initial tooth positions, patient information, case assessment information, or dental practitioner information, and receive suggested treatment strategies and a treatment plan based on the information provided.

Figure 5:
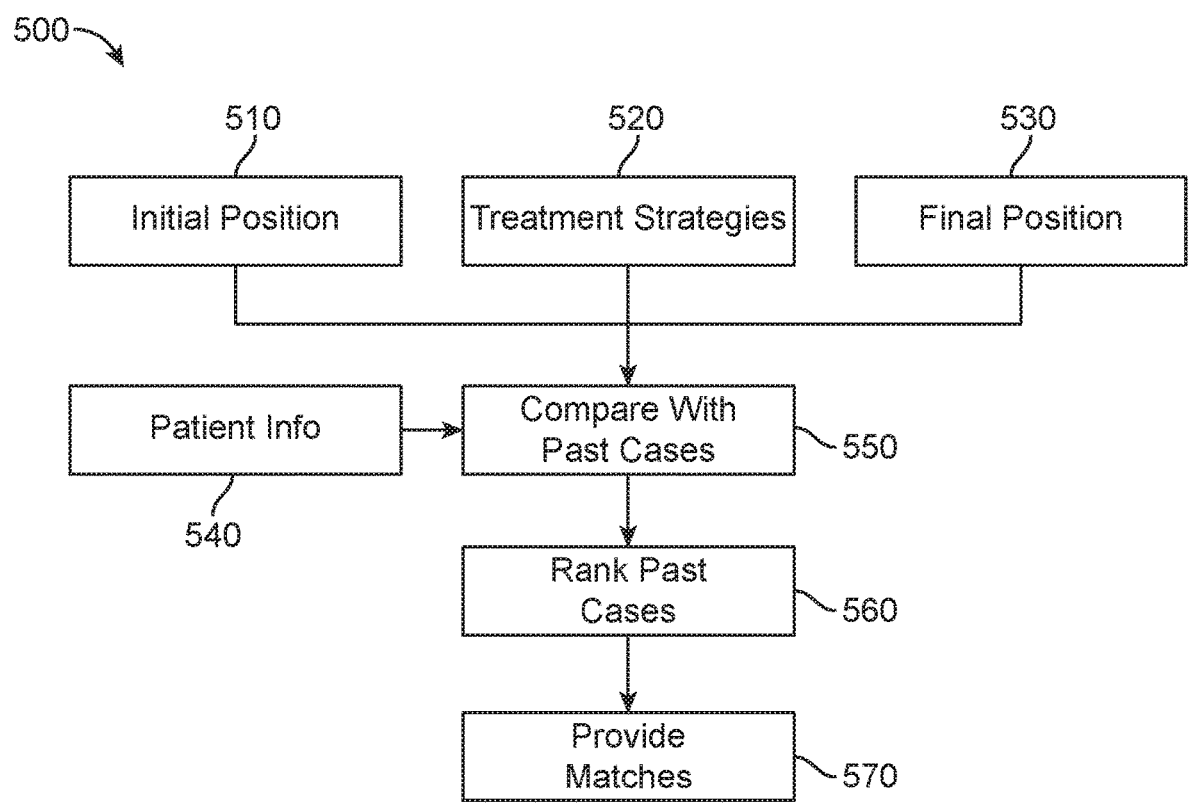
FIG. 5 illustrates a method of matching current cases with existing cases.
Figure 6:
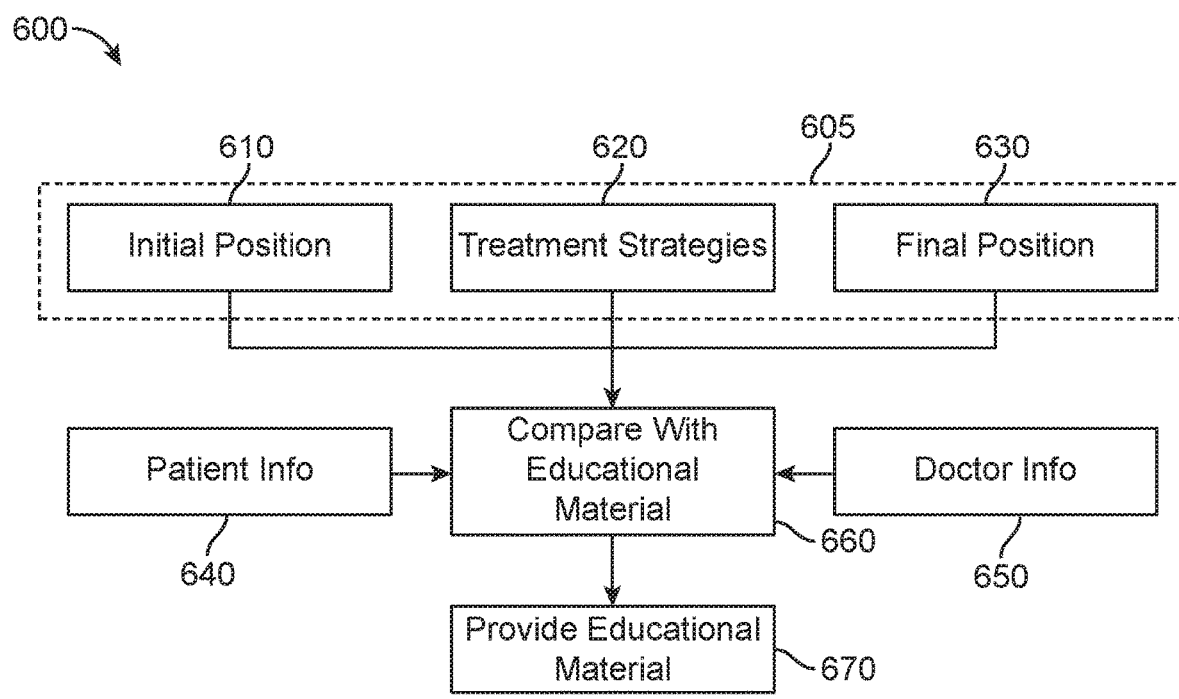
FIG. 6 illustrates a method of matching current cases with educational materials.

As shown in block 440, based on the one or more of the patient and treatment information, the case assessment, or the treatment plan, education and existing cases, including past and presently pending case assets are matched and then provided to the dental practitioner. FIGS. 5 and 6 provide additional details regarding the case and education matching.

As set forth above, appliances can be generated based on sequential planned arrangements of the patient's teeth and can be provided to the practitioner and ultimately administered to the patient at block 450. The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of treatment guidelines, or appliances and guidelines can be provided separately.

Referring to FIG. 5, a method 500 of matching existing cases with a current case is provided. At block 510 an initial position of a patient's teeth for a current case is provided. This can include obtaining data comprising an initial arrangement of the patient's teeth, which typically includes obtaining an impression or scan of the patient's teeth in their initial positions prior to the onset of treatment. In some embodiments, the patient's teeth are scanned directly while in others a mold or impression if formed from the patient's teeth and then the mold is scanned. For example, a plaster cast of the patient's teeth may be made using well known techniques. After the tooth casting is obtained, it can be digitally scanned using a conventional laser scanner or other range acquisition system to produce a digital model or data set of an initial position of the patient's teeth. The data set produced by the range acquisition system may, of course, be converted to other formats to be compatible with the software which is used for manipulating images within the data set. General techniques for producing plaster casts of teeth and generating digital models using laser scanning techniques are well known.

At block 520 treatment strategies for treating a patient's teeth for a current case are provided. The treatment strategies may include, for example, the staging of the movement of teeth in ordered steps to prevent collisions, tooth rotation or translation strategies, interproximal reduction of one or more teeth, and other treatment strategies such as, for example, tooth extraction, elastics use, attachment use, staging, and class II correction. In some embodiments, the treatment strategies may include strategies for treating creation conditions, such as excessive deep bite, open bite, or other conditions.

At block 530 a final or target position of a patient's teeth for a current case is provided. In some embodiments, a target tooth arrangement can be a planned final tooth arrangement selected for the patient's teeth at the end of all planned orthodontic treatment. In some embodiments, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

At block 540 patient information for a current case is provided. The patient information can include information such as patient demographic factors, such as age, gender, and race or patient tooth factors, such as tooth shape, tooth size, or morphology.

At block 550 a comparison is made between one or more of the initial position of a patient's teeth, treatment strategies for treating a patient's teeth, a final position of a patient's teeth, and patient information for a current case and a corresponding one or more of the initial position of a patient's teeth, treatment strategies for treating a patient's teeth, a final position of a patient's teeth, and patient information of a plurality of previous cases.

In some embodiments the degree of matching between the current case information and the case information for each of the plurality of previous cases is determined. In some embodiments, the factors may be binary, wherein a match is made or not made. For example, the sex of the patient may be either male or female and a match is therefore either made or not made depending on the sex of the current patient and the sex of the patient in the existing cases. In some embodiments, a match may be binary even when the factors and not a perfect match. For example, when matching the age of a patient, it may be desirable to include existing cases with patients that are within about 6 months of the age of the current patient or within about 1 year, 2 years, 3 years, or 5 years. In some embodiments an age match may be found when the age of the patient in the existing case is within about 1%, 2%, 5%, or 10% of the age of the current patient.

In some embodiments, a match may be binary based on a threshold. For example, when the position of one or more of the current patient's teeth are within 0.1 mm of the position of one of more of the corresponding teeth of a patient in an existing case, then a match may be made. In some embodiments, a match may be made when the position of one or more of the current patient's teeth are between 0.1 mm and 0.2 mm of the position of one of more of the corresponding teeth of a patient in an existing case or cases. In some embodiments, a match may be made when the position of one or more of the current patient's teeth are less than 0.05 mm, 0.2 mm, 0.3 mm, 0.4 mm, or 0.5 mm of the position of one of more of the corresponding teeth of a patient in an existing case.

In still other embodiments, the match may be a degree or percent match, for example on a scale between a minimum number and a maximum number. For example, with tooth position, a match between the position of a tooth of a current position with the position of a tooth of a past patient of less than 0.01 mm may be considered a 100% match or given a value of 100 (a maximum number), while a position difference of 1 mm or greater may be considered a 0% match or given a value of 0 (a minimum number), and position agreement of between 0.01 mm and 1 mm is assigned a value of between 100% (or 100) and 0% (or 0).

In this way, the information, such as initial position of a patient's tooth, the final position of a patient's tooth, the patient information, and the treatment strategies are compared between the current patient and each of a plurality of existing cases and a degree of match between the cases is assigned to each.

In some embodiments, also at block 550, the degree of match of the information and factors is averaged to determine an overall match for each of the existing cases with the current case.

In some embodiments, each factor or each piece of information, such as initial position of a tooth or set of teeth, the treatment strategies, the final position of a tooth or set of teeth, and the patient information is assigned a relative weight and a weighted average match for each of the existing cases with the current case is determined.

In some embodiments, some existing cases may be dropped from the comparison based on significant mismatch. For example, in some embodiments, only cases of the same sex, cases of adults, cases of teens, or cases of children, may be of interested. In such embodiments, once a mismatch between sex, age, race. etc. is determined, then comparison of that case can end and the case can be dropped from further analysis and ranking.

At block 560 the existing cases are ranked against each other in based on their comparison with the current case. For example, the cases may be ranked from highest to lowest average or weighted average.

In some embodiments, at block 560, the cases may be separated by a particular factor, such as treatment strategy. In such an embodiment, each of the cases may be separately ranked with respect to each treatment strategy.

At block 570 a selection of existing cases are provided to a dental practitioner. In some embodiments, the top 1, 2, 3, 4, or 5 existing cases may be provided to the practitioner based on the average or weighted after degree of match with the present case. In some embodiments, the top 1, 2, 3, 4, or 5, cases for each treatment strategy may be are provided to the practitioner based on the average or weighted after degree of match with the present case for each treatment strategy.

Providing the matched cases may include sending materials or information related to the case to a dental practitioner. For example, the materials for the existing case may include initial scans of the past patient's teeth, final scans of the past patient's teeth, intermediate scans of the past patient's teeth taken during treatment, treatment notes from the treating dental practitioner, and other medical and dental information related to the treatment of the patient in the existing case.

Referring to FIG. 6, a method 600 of matching education materials to a current case is provided. At block 605 case specifics are provided. Case specifics may include the initial position of a patients teeth, a final or target position of a patient's teeth, or treatment strategies proposed by the dental practitioner or a medical device provider, such as a provider of aligners or treatment plans.

At block 610 an initial position of a patient's teeth for a current case is provided. This can include obtaining data comprising an initial arrangement of the patient's teeth, which typically includes obtaining an impression or scan of the patient's teeth in their initial positions prior to the onset of treatment. In some embodiments, the patient's teeth are scanned directly via, for example, an intraoral scan, while in others a mold or impression if formed from the patient's teeth and then the mold is scanned. For example, a plaster cast of the patient's teeth may be made using well known techniques. After the tooth casting is obtained, it can be digitally scanned using a conventional laser scanner or other range acquisition system to produce a digital model or data set of an initial position of the patient's teeth. The data set produced by the range acquisition system may, of course, be converted to other formats to be compatible with the software which is used for manipulating images within the data set. General techniques for producing plaster casts of teeth and generating digital models using laser scanning techniques are well known.

At block 620 treatment strategies for treating a patient's teeth for a current case are provided. The treatment strategies may include, for example, the staging of the movement of teeth in ordered steps to prevent collisions, tooth rotation or translation strategies, interproximal reduction of one or more teeth, and other treatment strategies. In some embodiments, the treatment strategies may include strategies for treating creation conditions, such as excessive deep bite, open bite, or other conditions. In some embodiments the dental practitioner determines and provides the treatment strategies while in other embodiments, a system or medical device provider provides one or more treatment strategies.

At block 630 a final or target position of a patient's teeth for a current case is provided. In some embodiments, a target tooth arrangement can be a planned final tooth arrangement selected for the patient's teeth at the end of all planned orthodontic treatment. In some embodiments, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

At block 640 patient information for a current case is provided. The patient information can include information such as patient demographic factors, such as age, gender, and race or patient tooth factors, such as tooth shape, tooth size, or morphology.

At block 650 a dental practitioner's information is provided or received. The information may include past training and experience of the dental practitioner. For example, the types of training received and when the training was received, whether the practitioner is a general dental practitioner or a specialist, such as an orthodontist, the educational background of the dental practitioner, the types of cases the dental practitioner has handled the complexities of the cases the dental practitioner has handled, and the number of cases the dental practitioner has handled. In some embodiments, more recent information is proved, such as training received within the last 12 months is provided, while in some embodiments all training is provided.

In some embodiments, the medical equipment the dental practitioner has access to, such as access to an intraoral scanner is received.

In some embodiments, the location of the dental practitioner is received.

In some embodiments, information regarding the dental practitioner's past use of certain tools and resources is received. For example, information regarding the dental practitioner's review of previously provided treatment plans may be considered because, for example, a dental practitioner's interested in reviewing a treatment plan may indicate more advanced knowledge and understand of the tooth repositioning process. In some embodiments, the percentage of cases that are canceled over the lifetime of the dental practitioner or over the last 12 months is received. In some embodiments, the percentage of each type of case put on hold over the lifetime of the dental practitioner or over the last 12 months is received.

At block 660 the provided information and factors are compared and matched with available educational resources. In some embodiments, a dental practitioner's experience with particular procedures or case types is evaluated and if the dental practitioner could use additional educational material when handling such cases, then a match is determined. In some embodiments, educational material matches may be based on the equipment available to the dental practitioner. For example, if the dental practitioner does not have access to an intraoral scanner, then educational material may not be provided for the use of such a device. In some embodiments, education material may be provided for medical equipment not available to the dental practitioner in order to education the dental practitioner on the advantage of using a particular device, such as decreased length of office visits, increased accuracy in evaluating and diagnosing a patient, and other advantages.

In some embodiments, training material is matched to particular patient information, such as the sex, age, or race of the patient because different factors may influence how the patient should be treated and difficulties in treated certain types of patients.

In some embodiments, the case specifics, such as the treatment strategies proposed by the dental practitioner are considered and compared to a set of available treatment strategies for treating a particular condition. One or more of the available treatment strategies may have a high success rate, may be easier to preform, or may be more acceptable to some or a certain class of patients, then education materials directed to one of the other treatment strategies, such as one not selected by the dental practitioner, may be matched.

At block 670 matched educational resources are provided to the dental practitioner. Providing the education resources may include sending materials or information related to the case to a dental practitioner. For example, the materials case studies from existing cases, education materials and training for certain procedures or techniques, or training materials for how to use certain medical equipment or devices. The education resources may be training classes provided in real time to the dental practitioner or video or printed material provided to the dental practitioner.

Figure 7:
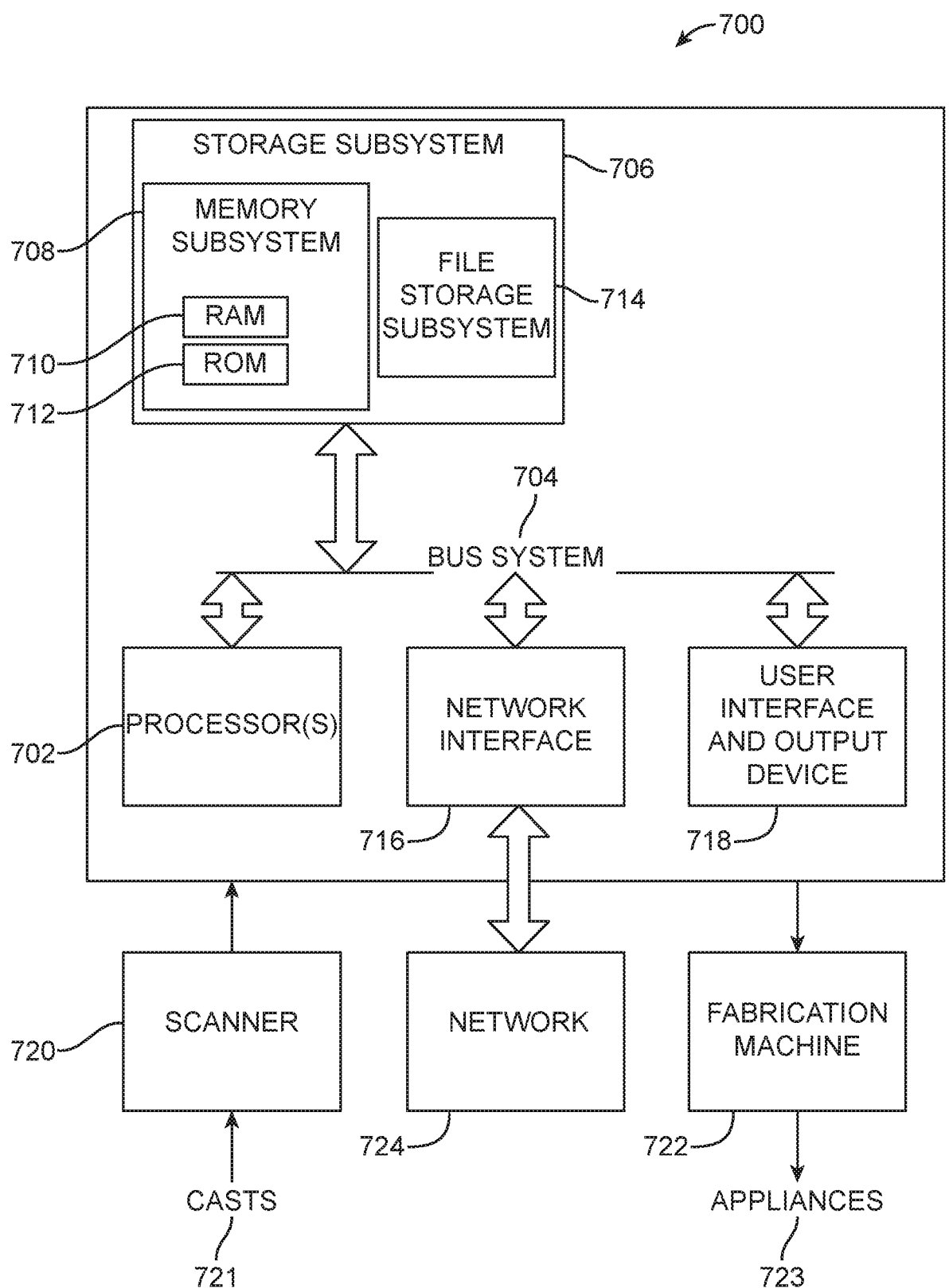
FIG. 7 is a simplified block diagram of a data processing system, in accordance with embodiments.

FIG. 7 is a simplified block diagram of a data processing system 700 that may be used in executing methods and processes described herein. The data processing system 700 typically includes at least one processor 702 that communicates with one or more peripheral devices via bus subsystem 704. These peripheral devices typically include a storage subsystem 706 (memory subsystem 708 and file storage subsystem 714), a set of user interface input and output devices 718, and an interface to outside networks 716. This interface is shown schematically as "Network Interface" block 716, and is coupled to corresponding interface devices in other data processing systems via communication network interface 724. Data processing system 700 can include, for example, one or more computers, such as a personal computer, workstation, mainframe, laptop, and the like.

The user interface input devices 718 are not limited to any particular device, and can typically include, for example, a keyboard, pointing device, mouse, scanner, interactive displays, touchpad, joysticks, etc. Similarly, various user interface output devices can be employed in a system of the disclosure, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically includes memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk. CD-ROM. DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining a digital representation (e.g., images, surface topography data, etc.) of a patient's teeth (e.g., by scanning physical models of the teeth such as casts 721, by scanning impressions taken of the teeth, or by directly scanning the intraoral cavity), which can be obtained either from the patient or from treating professional such as an orthodontist, and includes means of providing the digital representation to data processing system 700 for further processing. Scanner 720 may be located at a location remote with respect to other components of the system and can communicate image data and/or information to data processing system 1500, for example, via a network interface 724. Optionally, system 700 can include other input sources for obtaining patient data (e.g., CBCT data, ultrasound data, etc.). Fabrication system 722 fabricates appliances 723 based on a treatment plan, including data set information received from data processing system 700. Fabrication machine 722 can, for example, be located at a remote location and receive data set information from data processing system 700 via network interface 724.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A method for digital treatment planning to treat malocclusions of a patient's teeth, the method executed by a processor of a digital device, the method comprising:
   receiving current case information comprising:
      a digital model of an initial position of the patient's teeth,
      a plurality of treatment strategies for the patient's teeth, patient information related to the patient, and
      a digital model of a target position of the patient's teeth,
   wherein one or more of the plurality of treatment strategies are provided by a dental practitioner, and wherein each of the plurality of treatment strategies comprises a sequence of ordered steps of tooth movement from the initial position to the target position;
   comparing the current case information against past case information of past treatments of a plurality of existing cases, the past case information comprising: digital models of initial positions of the plurality of existing cases, digital models of target positions of the plurality of existing cases, and a plurality of treatment strategies of the plurality of existing cases, wherein comparing the current case information against the past case information comprises evaluating the plurality of treatment strategies for the patient's teeth against the plurality of treatment strategies of the plurality of existing cases; and
   ranking, based on the comparison, the past case information against the current case information to provide ranked past case information ranked by relevance to the current case information, wherein the ranked past case information comprises a ranking of past case information for each treatment strategy of the plurality of treatment strategies;

generating a treatment plan to reposition the patient's teeth towards the target position, the treatment plan comprising a plurality of intermediate tooth arrangements for moving the patient's teeth along a treatment path from the initial position toward the target position; and sending the ranked past case information and the treatment plan to the dental practitioner.

2. The method of claim 1, wherein:

the patient information related to the patient comprises patient factors for the patient, and wherein comparing the current case information against the past case information comprises matching the patient factors for the patient with patient factors of the plurality of existing cases.

3. The method of claim 2, wherein the patient factors include one or more of age, sex, ethnicity, and race.

4. The method of claim 2, wherein the patient factors include one or more of tooth shape, tooth size, tooth morphology, and arch shape.

5. The method of claim 1, wherein the plurality of treatment strategies for the patient's teeth include one or more of tooth extraction, elastics use, attachment use, and class II correction.

6. The method of claim 1, wherein the target position represents an intermediate position of the patient's teeth during treatment.

7. The method of claim 1, wherein the target position represents a desired position of the patient's teeth at completion of treatment.

8. The method of claim 1, wherein comparing the current case information against the past case information includes binary matching of at least one of the initial position of the patient's teeth, the target position of the patient's teeth, and the plurality of treatment strategies for the patient's teeth with initial positions, target positions, and treatment strategies of the plurality of existing cases.

9. The method of claim 1, wherein comparing the current case information against the past case information includes determining a degree of match of at least one of the initial position of the patient's teeth, the target position of the patient's teeth, and the plurality of treatment strategies for the patient's teeth with initial positions, target positions, and treatment strategies of the plurality of existing cases.

10. The method of claim 1, wherein comparing the current case information against the past case information includes averaging the degree of match of at least one of the initial position of the patient's teeth, the target position of the patient's teeth, and the plurality of treatment strategies for the patient's teeth with initial positions, target positions, and treatment strategies of the plurality of existing cases.

11. The method of claim 1, wherein ranking includes selecting one or more cases from the plurality of existing cases based on a respective ranking of each of the plurality of existing cases and providing the selected one or more cases of the plurality of existing cases to the dental practitioner.

12. The method of claim 1, further comprising providing to the dental practitioner at least three of the plurality of existing cases from the five highest ranked of the plurality of existing cases.

13. The method of claim 1, wherein comparing the current case information against the past case information comprises evaluating the digital model of the initial position of the patient's teeth against the digital models of initial positions of the plurality of existing cases, evaluating the digital model of the target position of the patient's teeth against the digital models of the target positions of the plurality of existing cases, or some combination thereof.

14. The method of claim 1, wherein comparing the current case information against the past case information comprises evaluating the patient information related to the patient against the past patient information related to the plurality of existing cases.

15. A system for treating malocclusions of a patient's teeth, the system comprising:

a processor;

a memory storage device comprising code that, when executed by the processor, causes the system to:

receive current case information comprising:

a digital model of an initial position of the patient's teeth, a plurality of treatment strategies for the patient's teeth, patient information related to the patient, and a digital model of a target position of the patient's teeth, wherein one or more of the plurality of treatment strategies are provided by a dental practitioner, and wherein each of the plurality of treatment strategies comprises a sequence of ordered steps of tooth movement from the initial position to the target position;

compare the current case information against past case information of past treatments of a plurality of existing cases, the past case information comprising: digital models of initial positions of the plurality of existing cases, digital models of target positions of the plurality of existing cases, and a plurality of treatment strategies of the plurality of existing cases, wherein comparing the current case information against the past case information comprises evaluating the plurality of treatment strategies for the patient's teeth against the plurality of treatment strategies of the plurality of existing cases; and rank, based on the comparison, the past case information against the current case information to provide ranked past case information ranked by relevance to the current case information, wherein the ranked past case information comprises a ranking of past case information for each treatment strategy of the plurality of treatment strategies;

generate a treatment plan to reposition the patient's teeth towards the target position, the treatment plan comprising a plurality of intermediate tooth arrangements for moving the patient's teeth along a treatment path from the initial position toward the target position; and send the ranked past case information and the treatment plan to the dental practitioner.

16. The system of claim 15, wherein the patient information related to the patient comprises patient factors for the patient, and wherein comparing the current case information against the past case information comprises matching the patient factors for the patient with patient factors of the plurality of existing cases.

17. The system of claim 16, wherein the patient factors include one or more of age, sex, ethnicity, and race.

18. The system of claim 16, wherein the patient factors include one or more of tooth shape, tooth size, tooth morphology, and arch shape.

19. The system of claim 15, wherein the target position represents an intermediate position of the patient's teeth during treatment or a desired position of the patient's teeth at completion of treatment.

20. The system of claim 15, wherein the code, when executed, further causes the system to rank the plurality of existing cases based on the matching and send to the dental practitioner at least three of the plurality of existing cases from the five highest ranked of the plurality of existing cases.

* * * * *